United States Patent [19]
Adamczyk, Jr. et al.

[11] Patent Number: 5,798,270
[45] Date of Patent: *Aug. 25, 1998

[54] ASSEMBLY AND METHOD FOR MONITORING HYDROCARBON CONCENTRATION IN EXHAUST GAS

[75] Inventors: Andrew A. Adamczyk, Jr.; James D. Pakko; Jeffrey S. Hepburn, all of Dearborn, Mich.

[73] Assignee: Ford Global Technologies, Inc., Dearborn, Mich.

[*] Notice: The term of this patent shall not extend beyond the expiration date of Pat. No. 5,524,433.

[21] Appl. No.: 694,721

[22] Filed: Aug. 9, 1996

[51] Int. Cl.[6] .................... C01B 17/16; G01N 33/00; G01N 7/00; F01N 3/00
[52] U.S. Cl. .................. 436/143; 423/230; 60/276; 60/277; 60/279; 60/297; 60/311; 73/232; 73/116
[58] Field of Search .................. 436/143; 60/279, 60/276, 311, 277, 297, 274; 423/230; 73/232, 116

[56] References Cited

U.S. PATENT DOCUMENTS

| 3,645,098 | 2/1972 | Templin et al. | 60/30 R |
|---|---|---|---|
| 3,674,441 | 7/1972 | Cole | 23/288 |
| 4,007,589 | 2/1977 | Neidhard et al. | 60/276 |
| 5,125,231 | 6/1992 | Patil et al. | 60/274 |
| 5,158,753 | 10/1992 | Take et al. | 422/173 |
| 5,179,833 | 1/1993 | Kuroda et al. | 60/276 |
| 5,214,915 | 6/1993 | Schneider et al. | 60/274 |
| 5,253,476 | 10/1993 | Levendis et al. | 60/279 |
| 5,259,189 | 11/1993 | Baier et al. | 60/274 |
| 5,379,586 | 1/1995 | Honji et al. | 60/276 |
| 5,524,443 | 6/1996 | Adamcyzk et al. | 60/276 |
| 5,622,682 | 4/1997 | Tom | 423/230 |

*Primary Examiner*—W. Gary Jones
*Assistant Examiner*—Ethan Whisenant
*Attorney, Agent, or Firm*—Peter Abolins, Esq.; Roger L. May, Esq

[57] ABSTRACT

A method of monitoring hydrocarbons concentration in an exhaust gas includes the steps of: sampling exhaust gas on a vehicle, isolating the hydrocarbons from the exhaust gas on a vehicle, and measuring the amount of hydrocarbons isolated from the sample on a vehicle and providing an indication based on the amount of hydrocarbons. A sensor assembly for monitoring the concentration of hydrocarbons in an exhaust gas of a vehicle includes: a hydrocarbon absorbing material placed in a stream of gas on a vehicle, a gas sensor operatively connected with the absorbing material and in the stream of gas and producing a gas signal, and a sensor controller connected to the gas sensor for receiving the gas signal and for determining the amount of hydrocarbons.

16 Claims, 5 Drawing Sheets

2

ASSEMBLY AND METHOD FOR MONITORING HYDROCARBON CONCENTRATION IN EXHAUST GAS

BACKGROUND OF THE INVENTION

1. Field of the Invention

The present invention relates generally to assemblies for monitoring emission system components and, more specifically to an assembly for monitoring hydrocarbon concentration levels in exhaust gas.

2. Description of the Related Art

Government legislation requires the implementation of on-board diagnostic systems for automobiles to monitor emission system components for the continued effective operation of the emission control system. The legislation states that the on-board diagnostic system must detect and warn the operator when the vehicle's tailpipe hydrocarbon levels exceed a designated value. In order to satisfy this requirement, a means for determining the hydrocarbon concentration in the vehicle exhaust is needed.

At the present time, there are no hydrocarbon measurement devices which are practical for on-board use. There has been some recent development of sensors which utilize a catalytic coating and temperature sensor to measure the rise in temperature due to the oxidation of the combustible components in the exhaust gas, but these calorimetric sensors are simultaneously sensitive to all combustible components, including carbon monoxide (CO) and hydrogen ($H_2$), as well as hydrocarbons.

Since there are currently no available means for directly determining the hydrocarbon concentration in the exhaust, conventional systems attempt to infer the hydrocarbon concentration through measurements of the operating characteristics of the various emission control components. For example, the oxygen storage capacity of the catalytic converter is monitored; this property is related to the catalyst's ability to convert hydrocarbons and is used to infer the hydrocarbon concentration in the exhaust. Unfortunately, these indirect methods for determining the hydrocarbon concentration in the exhaust are relatively inaccurate and have many other shortcomings. Thus, there is still a need in the art to directly measure hydrocarbon molecules in order to warn the operator and/or control the vehicle operation based on this information.

SUMMARY OF THE INVENTION

Accordingly, the present invention is a method of monitoring hydrocarbon concentration in an exhaust gas. The method includes the steps of sampling exhaust gas on a vehicle, isolating hydrocarbons from the sampled exhaust gas on the vehicle, and measuring the amount of hydrocarbons isolated from the sampled exhaust gas on the vehicle.

The present invention is also an assembly for monitoring hydrocarbons in exhaust gas on a vehicle. The assembly includes a hydrocarbon absorbing material placed in a stream of exhaust gas. The assembly also includes a gas sensor operatively connected with the absorbing material and in the stream of exhaust gas as to produce a gas signal, and a controller connected to the gas sensor for receiving the gas signal and for determining the amount of hydrocarbons in the stream of exhaust gas.

One advantage of the present invention is that the concentration of hydrocarbon molecules can be measured directly to monitor the effectiveness of the emission system. Another advantage of the present invention is that measurement of various emission components can be measured on board the vehicle.

Other features and advantages of the present invention will be readily appreciated as the same becomes better understood after reading the subsequent description taken in conjunction with the accompanying drawings.

DESCRIPTION OF THE PREFERRED EMBODIMENT(S)

Figure 1:
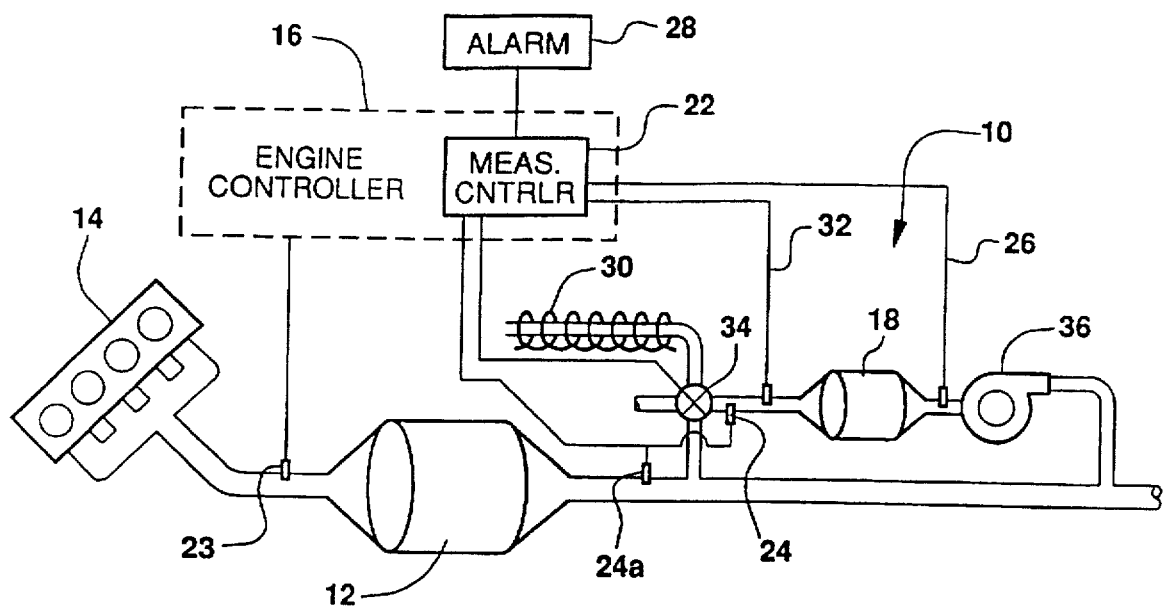
FIG. 1 is a schematic diagram of a first embodiment of an assembly for monitoring hydrocarbons in an exhaust gas according to the present invention.

Referring to the drawings, one embodiment of a sensor assembly 10 for monitoring hydrocarbon concentration in the exhaust gas of a vehicle (not shown) is generally illustrated in FIG. 1. The sensor assembly 10 is placed in a location downstream from a catalytic converter 12 used in conjunction with and receiving emissions from an engine 14 of the vehicle. The vehicle also includes an engine controller 16 which is common in the art and used to monitor the exhaust gas for engine fuel control.

The sensor assembly 10 is connected downstream from the catalytic converter 12 to determine the concentration of emission system components, and more particularly hydrocarbons. The sensor assembly 10 includes a hydrocarbon absorbing material 18 which is placed in a stream of the exhaust gas, a gas sensor apparatus 20 operatively connected with the absorbing material 18 and in the stream of exhaust gas to produce gas signals, and a measuring controller 22 connected to the gas sensor apparatus 20 for receiving the gas signal and for determining the amount of hydrocarbons or any other selected exhaust gas component.

The gas sensor apparatus 20 includes an upstream sensor 24 which is upstream of the absorbing material 18 producing an upstream signal, and a downstream sensor 26 which is positioned downstream of the absorbing material 18 producing a downstream signal. The measuring controller 22 receives the upstream and downstream signals and determines a difference between the signals, providing an amount or concentration of hydrocarbons in the exhaust gas. The measuring controller 22 may be connected to an alarm 28 for receiving the difference and providing an indication when the difference has a predetermined relationship to a preset value. The measuring controller 22 may be formed as a part of the engine controller 16. It should be appreciated that the alarm 28 may be in an occupant compartment of the vehicle to allow indication to the operator or tester.

The absorbing material 18 is characteristically sensitive to hydrocarbons while being insensitive or rejecting hydrogen and carbon monoxide components. The absorbing material 18 has been found to suitably include any of the following: zeolite, an activated carbon, or a pillared clay, all in the form of a particle bed, a coated honeycomb monolith, or a coated wafer. These absorbing materials 18 remove substantially only hydrocarbons from the exhaust gas. It should be appreciated that other absorbing materials may be used depending on the exhaust gas component desired to be measured.

The upstream and downstream sensors 24, 26 may include any of the following types: universal exhaust gas oxygen sensor (UEGO), heated exhaust gas oxygen sensor (HEGO), exhaust gas oxygen sensor (EGO), calorimetric sensors, or other combustible sensors.

High temperatures have been known to inhibit absorption of hydrocarbons in the absorbing materials 18 considered. Therefore, a temperature sensor 32 may be used to send a temperature signal to the measuring controller 22 to allow compensation of the hydrocarbon measurements. Less absorption of exhaust gas components occurs as the temperature increases. Alternatively, a heat exchanger (not shown) may be used to cool the sampled exhaust gases where they are introduced into the absorbing material 18.

A valve 34 is utilized to control a source of air (not shown) through the absorbing material 18, and a pump 36 is utilized to draw the exhaust gas through the absorbing material 18. The valve 34 alternately directs sampled exhaust gas, heated air and ambient air through the absorbing material 18. The exhaust gas is drawn through the absorbing material 18 so that hydrocarbons (or any other selected exhaust gas component) is absorbed thereby, allowing the remaining components to pass therethrough. The heated air removes the hydrocarbons and "cleans" the absorbing material 18 for the next test. The ambient air cools the absorbing material 18 so that maximum absorption can occur. It should also be appreciated that alternative means of heating the absorbing material 18 would be known by one skilled in the art, such as by electrical current through a resistive element embedded in the absorber or through chemical reaction, etc., which "cleans" the absorbing material 18 for a subsequent test.

Furthermore, the upstream gas sensor 24, 24a has two alternate locations as shown in FIG. 1. The preferred location has the upstream sensor 24 exposed only to the sample gas which may be optimum for hydrocarbon measurement. However, an alternate location is in the bulk exhaust gas stream, which sensor 24a may also be used by the measuring controller 22 in concert with the upstream sensor 23 of the catalytic converter for engine fuel control. The measuring controller 22 uses the outputs from the gas sensors 24,26 located upstream and downstream of the absorbing material 18, along with the sample temperature, to deduce the exhaust gas hydrocarbon concentration.

A method, according to the present invention, for monitoring the amount of hydrocarbons is carried out by the assembly 10 in FIG. 1 and controlled by the measuring controller 22 includes the following steps. The exhaust gas is sampled on the vehicle by movement of the valve 34 to the proper position to allow exhaust gas to pass, and hydrocarbons are isolated from the sample on the vehicle by the absorbing material 18. The pump 36 is turned on and the valve 34 rotated so that exhaust gas may be sampled and drawn through the absorbing material 18 by the pump 36. The upstream and downstream sensors 24, 26 concurrently measures the components of the exhaust gas by determining the amount of absorption of a selected component, e.g. hydrocarbon, by the absorbing material 18. Both sensors 24, 26 send a signal to the measuring controller 22. From the signals, the measuring controller 22 can determine the amount of hydrocarbons in the exhaust gas by taking the difference between the upstream and downstream sensors 24, 26. If this difference level exceeds a predetermined relationship with a preset value, the on-board alarm 28 can be sounded or indicated otherwise, to the user or tester of the vehicle. Such indication may occur when the concentration level is one and one-half times its original value when new. This will indicate that the exhaust or emission system needs reconditioning.

Once the readings have been taken, the absorbing material 18 will need to be purged or cleaned for a new test. This may be accomplished by heating the absorbing material 18. The heating may be provided by an electrical heater 30 used to heat air which is drawn through the absorbing material 18 by switching of the valve 34 appropriately for removing hydrocarbons therefrom. The electrical heater 30 may then be turned off allowing ambient air to flow therethrough to cool the absorbing material 18. It is thereafter necessary to flow through ambient air to cool the absorbing material 18 for a subsequent test, which is also switched by the valve 34.

Figure 2:
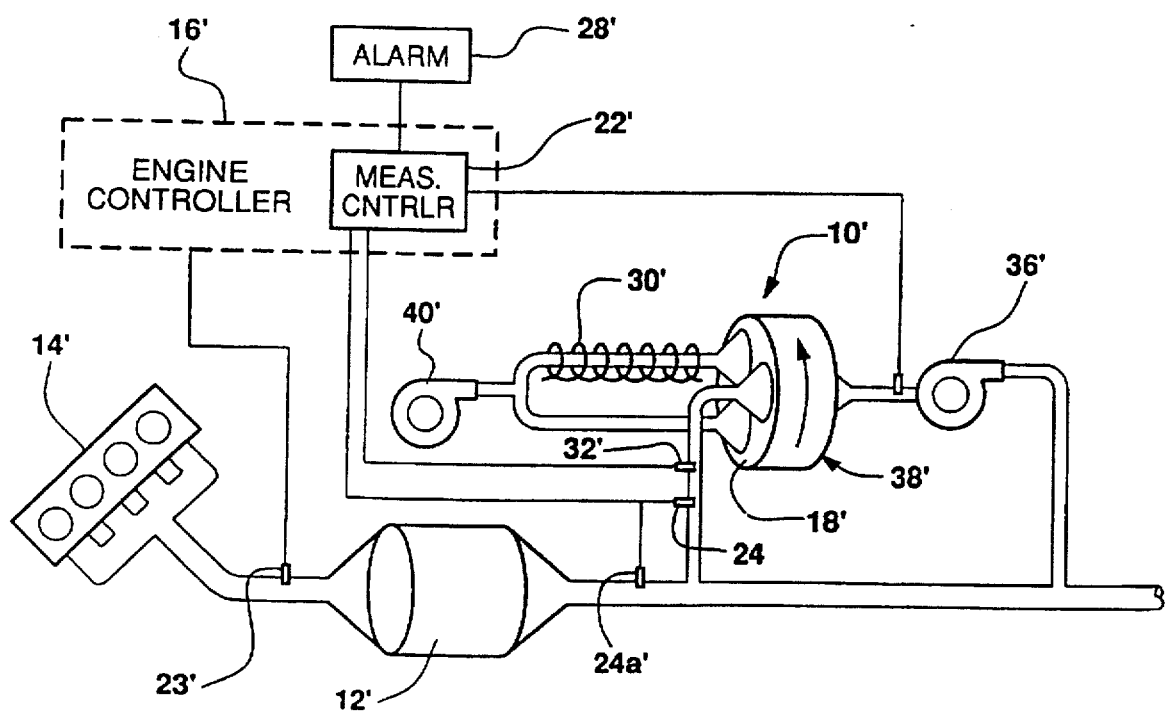
FIG. 2 is a schematic diagram of a second embodiment of the assembly of FIG. 1.
Figure 3:
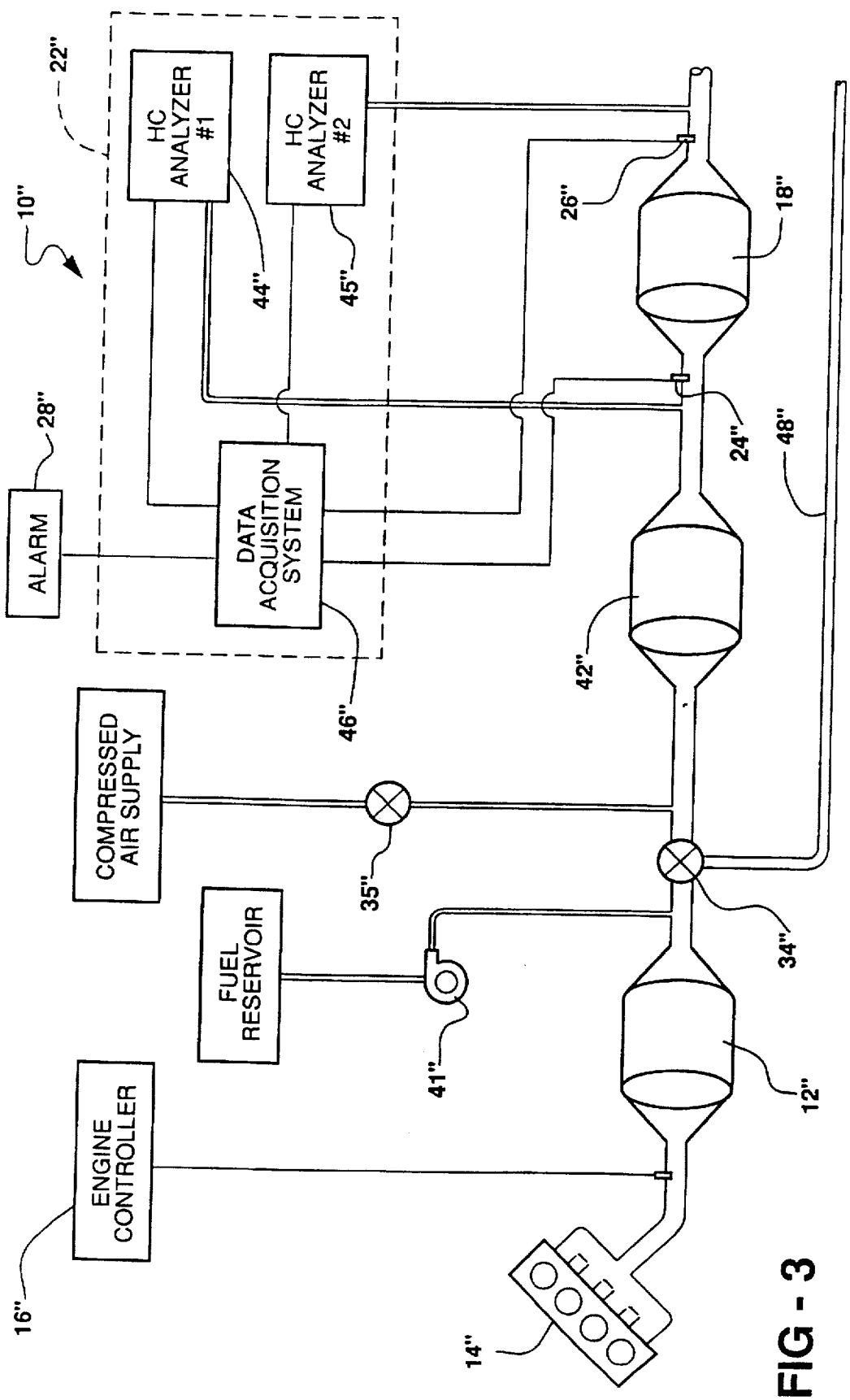
FIG. 3 is a schematic diagram of a third embodiment of the assembly of FIG. 1.

FIGS. 2 and 3 illustrate second and third embodiments, respectively, of the assembly 10 of FIG. 1. Similar primed reference numerals are used to indicate like parts.

FIG. 2 operates similar to FIG. 1 except that the absorbing material 18' is provided on a rotating substrate 38' which rotates in the direction shown in FIG. 2. Therefore, each element of the absorbing material 18' is exposed alternately to the exhaust gas, heated air, and ambient air for continuous and simultaneous measurement and reconditioning. In this embodiment, separate pumps 36', 40' are required for the exhaust gas and the cleansing air, respectively. The method is the same as the method in the first embodiment except for the continuous measurement.

In the third embodiment, the assembly 10" was tested to verify the sampling of only hydrocarbons. Instead of sampling a portion of the exhaust gas, all of the exhaust gas is passed through the assembly 10". While the measuring controller 22 maintains a stoichiometric air/fuel ratio, the engine 14 is operated at a constant speed and load. Exhaust gas is first passed through the catalytic converter 12" to oxidize the hydrocarbons. After the catalytic converter 12", a pump 41" is used to introduce gasoline directly into the exhaust gas, allowing the hydrocarbon concentration of the exhaust to be manipulated for the test. An uncoated ceramic monolith 42" is used upstream of the absorbing material 18" to cool the exhaust gas. The assembly 10" has the UEGO sensors 24", 26" placed upstream and downstream of the absorbing material 18", which is a ceramic monolith coated with zeolite material that has an affinity for absorbing hydrocarbons. Conventional laboratory hydrocarbon analyzers 44", 45" measure the hydrocarbon concentration both upstream and downstream of the absorbing material 18". A data acquisition system or computer 46" receives the data from the analyzers 44", 45", all acting as the measuring controller 22" in this embodiment. The valve 34" directs either the flow through the absorbing material 18" or through the bypass path 48". The test was initiated by moving the bypass valve 34" to bypass the exhaust, and the pump 41" was adjusted to provide the desired exhaust hydrocarbon concentration. The bypass valve 31" was then switched to introduce exhaust gas to the assembly 10" to begin the test. The data acquisition system 46" continuously records the output of the sensors 24", 26" and analyzers 44", 45". The pump 41" is then turned off and clean exhaust gas is used to remove the accumulated hydrocarbons from the zeolite absorbing material 18". Ambient air is passed over the absorbing material 18" to cool it in preparation for the next test by opening the valve 35". The test is then repeated with a different pump setting, resulting in different exhaust hydrocarbon concentrations.

Figure 4:
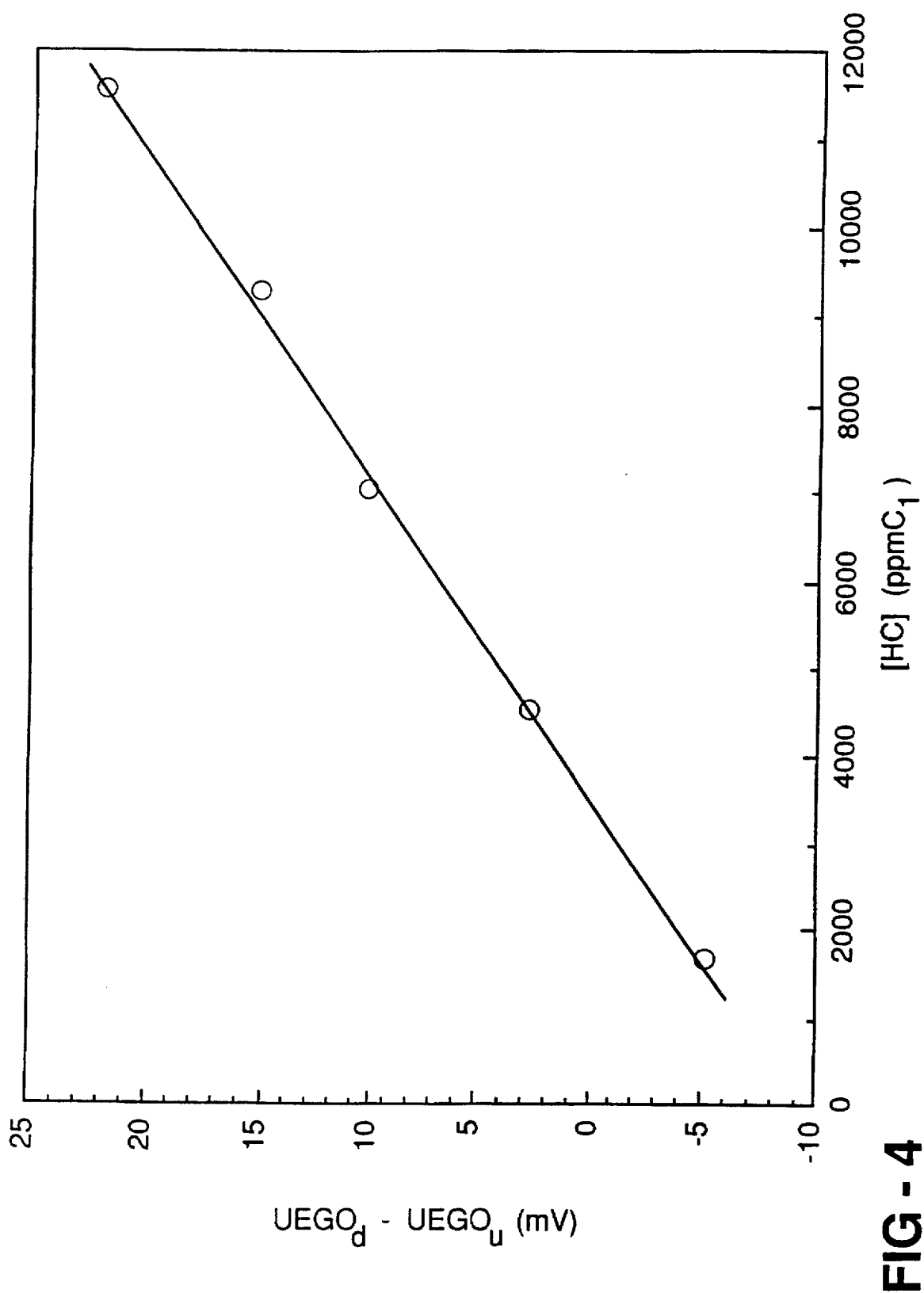
FIG. 4 is a graph illustrating linear correlation between hydrocarbon concentration and difference in sensed signals of the assembly of FIG. 3.

The difference in the sensor outputs measured about 30–35 seconds after the exhaust was first introduced to the assembly 10" was correlated with the exhaust gas hydrocarbon concentration for the test. FIG. 4 shows the results of the test. The output of the downstream sensor 26" minus that of the upstream sensor 24" is plotted as a function of exhaust gas hydrocarbon concentration, upstream of the assembly 10". The experimental data is marked by circles, and regression analysis of these data yields the straight line as illustrated. This shows the direct linear correlation between the differences of the sensor signals with hydrocarbon concentration. The Y-intercept of the fitted line is non zero since the response of the sensors does tend to vary from sensor to sensor. The difference could be compensated for by allowing the absorbing material 18" to be saturated. Since the upstream and downstream hydrocarbon concentration would then be the same, the zero point could be obtained.

Figure 5:
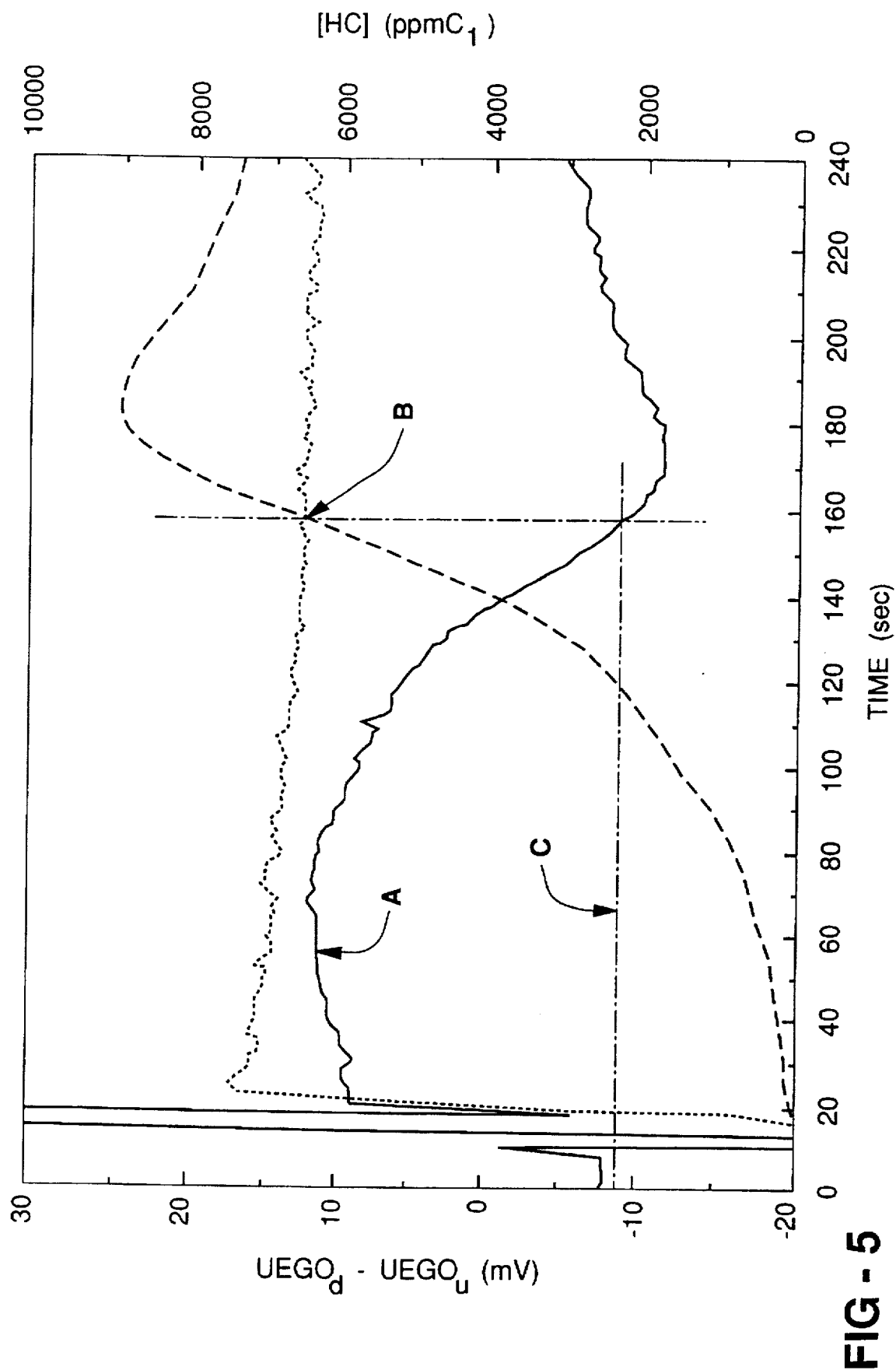
FIG. 5 illustrates sensor signal outputs of the assembly at FIG. 3.

FIG. 5 shows the hydrocarbon concentration both upstream and downstream of the absorbing material 18" along with the difference in sensed signals throughout the test. The data in FIG. 4 was obtained with the time period marked A. It was shown that the zeolite is very effective in removing hydrocarbons during in this period, and that the downstream hydrocarbon concentration is very low. Therefore the output of the assembly 10" is a function of the upstream hydrocarbon. The point at which the zeolite becomes saturated, and the downstream hydrocarbon concentration exceeds the upstream hydrocarbon concentration is marked as the hydrocarbon cross over time B. At this time, the output C of the assembly 10" is nearly equal to the zero intercepts of the line shown in FIG. 4. In addition to this test, a test was performed using these same conditions, except that prior to the test, the zeolite was loaded with hydrocarbons, and the reconditioning was not performed. This simulated the operation of assembly 10" in which the absorbing material 18" had been degraded. This data shows that the hydrocarbon cross over time is significantly less than for the reconditioned zeolite absorbing material 18". Therefore, the hydrocarbon cross over time may be used for a criteria for detecting an inoperative condition of the assembly 10" and to indicate the alarm 28".

Figure 6:
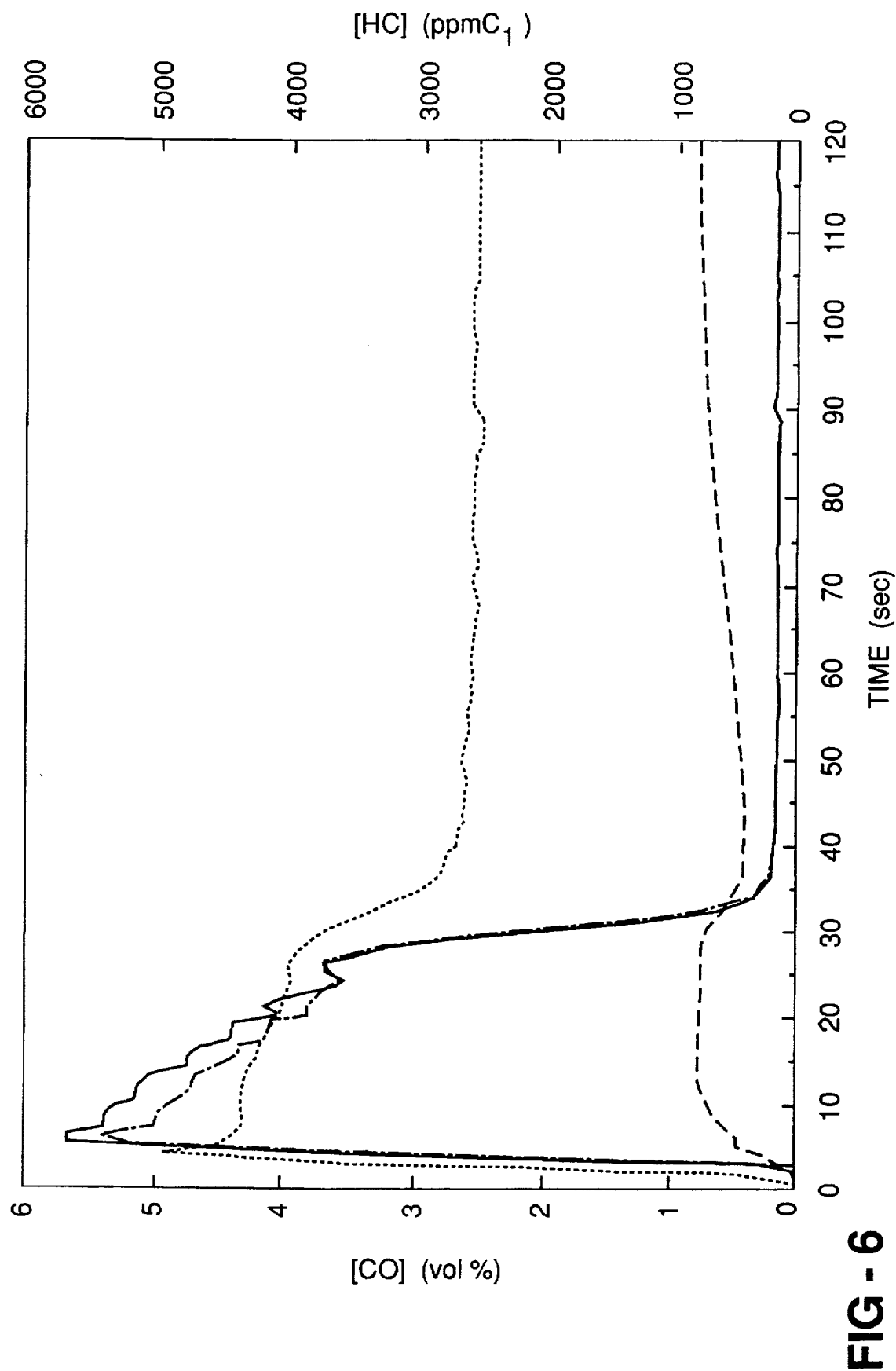
FIG. 6 is a graph illustrating hydrocarbon and CO concentrations measurements before and after the absorbing material in the exhaust gas stream of the assembly of FIG. 3.

FIG. 6 shows the hydrocarbon and the CO concentration measured before and after the zeolite absorbing material 18" in an exhaust gas stream. The hydrocarbons are shown to be removed very effectively while little or no CO is removed. This demonstrates that the assembly 10" is not sensitive to CO.

Since the overall assembly 10" is directly related to exhaust gas hydrocarbon concentration, and not a combination of hydrocarbon, CO and $H_2$, a "true" hydrocarbon exhaust system sensor specified by the on-board diagnostic legislation has been developed. Rather than measuring an indirect property, such as $O_2$ storage and relating it to hydrocarbon performance, the assembly 10, 10', 10" can measure hydrocarbon concentration directly.

The present invention has been described in an illustrative manner. It is to be understood that the terminology which has been used is intended to be in the nature of words of description rather than of limitation.

Many modifications and variations of the present invention are possible in light of the above teachings. Therefore, within the scope of the appended claims, the present invention may be practiced other than as specifically described.

What is claimed is:

1. A method of monitoring hydrocarbon concentration in exhaust gas on a vehicle comprising the steps of:

selectively sampling exhaust gas on an operating vehicle containing a variety of chemicals;

isolating hydrocarbons from the sampled exhaust gas on the vehicle;

directly measuring an amount of hydrocarbons isolated from the sampled exhaust gas on the vehicle by directly sensing the presence of hydrocarbons in the sampled exhaust gas and providing an indication based on the amount of hydrocarbons;

the step of measuring includes measuring the sampled exhaust gas before the step of isolating the hydrocarbons producing an upstream signal and measuring the sampled exhaust gas after the step of isolating the hydrocarbons producing a downstream signal, and determining the difference between the upstream and downstream signals the difference representing the amount of hydrocarbons.

2. A method as set forth in claim 1 wherein the step of isolating comprises absorbing the hydrocarbons in an absorption material which rejects hydrogen and carbon monoxide.

3. A method as set forth in claim 2 including the step of heating the absorption material to remove hydrocarbons therefrom.

4. A method as set forth in claim 3 including the step of cooling the absorption material for subsequent absorption.

5. A method as set forth in claim 1 including the step of producing a alarm signal when the amount of hydrocarbons reaches a predetermined amount.

6. A sensor assembly for monitoring the concentration of hydrocarbons in an exhaust gas on a vehicle comprising:

a hydrocarbon absorbing material placed in a stream of exhaust gas on a vehicle;

a gas sensor operatively connected with said hydrocarbon absorbing material and in the stream of exhaust gas on the vehicle to produce a gas signal, said gas sensor including an upstream sensor positioned upstream of said absorbing material in the stream of exhaust gas producing an upstream signal and a downstream sensor positioned downstream of said absorbing material in the stream of exhaust gas producing a downstream signal; and a sensor controller on the vehicle connected to said gas sensor for selectively receiving said gas signal and for determining the amount of hydrocarbons based on a difference between said upstream signal and said downstream signal.

7. An assembly as set forth in claim 6 wherein said gas sensors comprise exhaust gas oxygen sensors.

8. An assembly as set forth in claim 6 wherein said sensor controller includes a measuring controller for determining the difference between the upstream and downstream signals providing the amount of hydrocarbons.

9. An assembly as set forth in claim 6 wherein said sensor controller includes an alarm for receiving the difference and providing indication when the difference has a predetermined relationship to a preset value.

10. A method of monitoring exhaust gas components on a vehicle, comprising the step of:

selectively sampling exhaust emissions on an operating vehicle;

isolating a selected component from the sample on the vehicle; and directly measuring an amount of the selected component isolated from the sample on the vehicle by measuring the exhaust sample before the step of isolating the hydrocarbons producing an upstream signal and measuring the exhaust sample after the step of isolating the selected component producing a downstream signal, and determining the difference between the upstream and downstream signals, the different representing the amount of the selected component.

11. A method as set forth in claim 10 wherein the step of isolating comprises absorbing the selected component in an absorption material which is sensitive only to the selected material and which rejects non-selected components.

12. A method as set forth in claim 10 including the step of producing an alarm signal when the amount of the selected component reaches a predetermined amount.

13. A method as set forth in claim 1 including the step of selectively during the operation of the vehicle sampling, isolating, and measuring the amount of hydrocarbons.

14. An assembly as set forth in claim 6 wherein said sensor controller is connected on the vehicle and controls engine fuel ratio.

15. A method as set forth in claim 10 including the step of selectively during the operation of the vehicle sampling, isolating, and measuring the amount of the selected component.

16. A method of monitoring hydrocarbon concentration in exhaust gas on a vehicle comprising the steps of:
sampling exhaust gas on a vehicle;
isolating hydrocarbons from the sampled exhaust gas on the vehicle;
measuring an amount of hydrocarbons isolated from the sampled exhaust gas on the vehicle and providing an indication based on the amount of hydrocarbons;
the step of producing an alarm signal when the amount of hydrocarbons reaches a predetermined amount.

* * * * *